US008287776B2

(12) United States Patent
Maurer et al.

(10) Patent No.: US 8,287,776 B2
(45) Date of Patent: Oct. 16, 2012

(54) PREPARATION OF A PHOTOCHROMIC INK

(75) Inventors: Marc Maurer, Village-Neuf (FR); Max Hügin, Rünenberg (CH); Thomas Raimann, Sisseln (CH); Leonhard Feiler, Binzen (DE); Bruno Inderbitzin, Bouxwiller (FR); André Fuchs, Schliengen-Obereggenen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/141,718

(22) PCT Filed: Dec. 23, 2009

(86) PCT No.: PCT/EP2009/067825
§ 371 (c)(1),
(2), (4) Date: Aug. 17, 2011

(87) PCT Pub. No.: WO2010/079098
PCT Pub. Date: Jul. 15, 2010

(65) Prior Publication Data
US 2011/0297898 A1 Dec. 8, 2011

(30) Foreign Application Priority Data
Jan. 8, 2009 (EP) .................................. 09150214

(51) Int. Cl.
*G02B 5/23* (2006.01)
*G01N 33/00* (2006.01)
(52) U.S. Cl. ........ 252/586; 116/201; 252/582; 427/160; 427/337; 427/544; 436/92; 523/161; 548/409
(58) Field of Classification Search ................ 282/582, 282/586; 116/201; 347/52; 427/288, 331, 427/337, 384, 544, 160; 430/19, 270.15, 430/905; 503/200, 217; 252/582, 586; 436/92; 523/161; 548/409
See application file for complete search history.

(56) References Cited

U.S. PATENT DOCUMENTS

| 3,964,911 | A | * | 6/1976 | Robillard ..................... 430/147 |
| 3,999,989 | A | | 12/1976 | Ono |
| 5,633,109 | A | | 5/1997 | Jennings |
| 7,718,325 | B2 | * | 5/2010 | Norsten et al. ................. 430/19 |
| 8,007,900 | B2 | | 8/2011 | Hoekstra et al. |
| 2003/0002132 | A1 | | 1/2003 | Foucher et al. |
| 2007/0172951 | A1 | | 7/2007 | Levy |
| 2010/0043695 | A1 | | 2/2010 | Reichert et al. |
| 2010/0135353 | A1 | | 6/2010 | Fuchs et al. |
| 2011/0059545 | A1 | | 3/2011 | Salman et al. |
| 2011/0139059 | A1 | | 6/2011 | Feiler et al. |

FOREIGN PATENT DOCUMENTS
EP 1260560 A 11/2002
WO WO2005/075978 A2 * 8/2005

OTHER PUBLICATIONS

Copending U.S. Appl. No. 13/098,541, filed May 2, 2011.
Copending U.S. Appl. No. 13/141,721, filed Jun. 23, 2011.
Copending U.S. Appl. No. 13/146,230, filed Jul. 26, 2011.
Galbertshtam et al., Chem. of Heterocyclic Compounds vol. 12, Jan. 1, 1977, pp. 1309-1313.
Filley et al. Journal of Photochemistry and Photobiology vol. 117, Jan. 1, 1998 pp. 193-198.
Gugava et al., Proceedings of the Academy of Sciences of the Georgian SSR, vol. 8, No. 4, Jan. 1, 1982 pp. 288-293.
Pantsyrnyi et al., Chem. Of Heterocyclic compounds, vol. 7, No. 1, Jan. 1, 1971, p. 134.

* cited by examiner

*Primary Examiner* — Bijan Ahvazi
(74) *Attorney, Agent, or Firm* — Shiela A. Loggins

(57) ABSTRACT

The present invention relates to a photochromic ink, the process for its preparation which is based on a spiropyran powder obtainable by melting, cooling and crushing, and to a new form of a spiropyran obtainable thereby. Said process to prepare a photochromic ink comprises the steps of a) heating and melting the spiropyran at a temperature below 250 C, b) cooling the melt to obtain a solidified spiropyran, c) crushing the solidified spiropyran to obtain a powder, d) optionally adding the powder to a binder providing the basis for the photochromic ink.

6 Claims, No Drawings

PREPARATION OF A PHOTOCHROMIC INK

The present invention relates to a photochromic ink, the process for its preparation which is based on a photochromic spiropyran powder obtainable by melting, cooling and crushing, and to a new form of a photochromic spiropyran obtainable thereby.

The use of photochromic inks or dyes is well known. By "photochromic ink" is meant a formulation formed as fluid ink which changes color when exposed to UV light radiation and provides a sufficiently high color density for use in the printing processes.

The International Application WO2005075978 (Freshpoint) describes the preparation of solvent-based or water-based printing inks comprising a spiropyran, an acrylate polymer as binder, a solvent or water and additives. The spiropyran is added as finely ground powder.

Spiropyrans used for preparing printing inks for time temperature indicators have to be easily dispersible. Therefore a small particle size of the spiropyran is required, for example obtained by intensively milling using standard bead mills. This method has at least two drawbacks. First, the milling operation is a time-intensive process, as long milling times are required to produce small enough particles to enable the formation of a stable dispersion. Second, the milling operation can not be used for all spiropyrans as some spiropyrans irreversibly change their color during milling.

A good dispersibility is needed to obtain a high color strength. The use in aqueous and solvent-based systems is desired.

The problem underlying the present invention is to reduce the milling time and to prepare an easily activable spiropyran which can be easily converted into a colored spiropyran having a high color strength. "Easily activable" or "easily converted" means that only short exposure to UV light is required.

It has been found that spiropyrans after melting and re-solidifying show different properties compared to crushed spiropyrans obtained by milling. First, it is possible to combine the spiropyran powder with a basic ink formulation without intensive milling. Second, a very high color strength is obtained after activation with UV light. In order to reach the same color strength milled spiropyrans need a longer exposure time (circa 10 times longer) with UV light than the melted/re-solidified products.

Thus, the invention relates to a process to prepare a photochromic ink comprising the steps of
a) heating and melting a spiropyran, i.e. a photochromic spiropyran at a temperature below 250° C., i.e. heating a photochromic spiropyran until it has melted,
b) cooling the melt to obtain a solidified spiropyran,
c) crushing the solidified spiropyran to obtain a powder,
d) optionally adding the powder to a binder providing the basis for the photochromic ink.

The invention further relates to a photochromic ink obtainable according to the process of claim 1.

The invention further relates to a photochromic spiropyran in the form of a powder which, after dispersion in a printing ink, has at least the double color strength than known forms of the same spiropyran, said powder being obtainable by
a) heating and melting a photochromic spiropyran at a temperature below 250° C., i.e. carefully heating the spiropyran until it has melted,
b) cooling the melt to obtain a solidified spiropyran, and
c) crushing the solidified spiropyran to obtain a powder.

The reason for the unique property of the new form of a spiropyran is not entirely clear. It may be due to the particle size. Spiropyrans of similar particle size may e.g. not be accessible by conventional methods due to reaggregation of small particles in the milling operation.

The inventive process allows the preparation of easily activable time temperature indicators in powder form which can be used in various ink formulations.

The decomposition temperature of spiropyrans is below 250° C., i.e. all spiropyrans so far tested by the present inventors at least start decomposing below or even far below 250° C. A certain degree, e.g. up to 20%, 30%, 40% or even 50%, of decomposition is acceptable since the gain in color strength by the inventive process more than compensates for the loss of intact spiropyrans by decomposition. However, some spiropyrans tend to decompose rather rapidly, some even explosively. Hence, due care should be taken not to raise the temperature more than is necessary to obtain a complete melt or not to use explosive spiropyrans in the process of the present invention, especially not in larger scale. Spiropyrans which are suitable for being used in the process of the present invention can easily be detected and selected, e.g. by heating an undangerously small amount of them until they melt and watching the decomposition behaviour.

The preferred manner of carrying out process step a) above is to heat the spiropyran until it has melted, i.e. to heat it only slightly, e.g. 2, 5 or 10° C. above its melting point which is usually in the range of 140-200° C., especially 150-190° C. Preferably, heating is continued until melting is complete, i.e. all of the spiropyran has melted, but in order to avoid circumvention of the patent protection the respective patent claim comprises also those modifications of the process wherein only a substantial portion, e.g. 10, 20, 30, 40, 50, 60, 70, 80 or 90 percent (percent), of the spiropyran has melted.

The solidified spiropyran is in a transparent form.

Solidified is crystalline or semi amorphous. The term "semi-amorphous" herein means a spiropyran having an intermediate structure of an amorphous structure and a crystalline structure.

Cooling means, for example, cooling to room temperature or a temperature below room temperature and comprises also shock cooling. Shock cooling is preferably performed by pouring the melt on solid carbon dioxide (also called dry ice or carbon dioxide snow) or into liquid nitrogen whereupon the melt usually splits into tiny pieces.

The melting is carried out using any method of heat transfer, for example the melting is formed by heating using an oil bath, by melt extrusion, by radiation, e.g. NIR/IR radiation, heating using a hot air technology, heating by using a cold plasma and the like.

A short heating treatment is preferred to avoid the decomposition of the spiropyrans.

Polymeric binders for inks include all polymers known to be used in inks, e.g. homopolymers, copolymers (random or block-copolymers) or mixtures thereof including polymers of acrylic acid or methacrylic acid, acrylates or methacrylates (e.g. methyl acrylate or methyl methacrylate), styrene, acrylamide, vinyl acetate, vinyl alcohol, vinyl chloride, polyurethanes, cellulose nitrate, carboxymethyl cellulose. Preferred is a water-soluble or water-dispersible acrylic polymer. The binder is thus preferably an acrylic binder.

Inks contain a variety of additives to eliminate foaming, dispersion of pigments, rheological modifiers, and slip agents.

The inks comprise a total content of spiropyran of from 1 to 20% by weight, preferably 1.5-20% by weight, 2-20% by weight, 3-20% by weight based on the total weight of the ink.

The spiropyran-dispersed ink composition can be produced by employing various methods which have so far conventionally been known. For example, it can readily be obtained by blending the respective components (binder, additive, spiropyran powder) and mixing and stirring them by means of a stirrer such as a dissolver or mixing and crushing them by means of a ball mill.

The spiropyran compound is for example a spiropyran as disclosed (including processes for its manufacture) in WO 2008/083925 A1 or WO 2005075978 A2 (Freshpoint), or a spiropyran as disclosed in the European Application EP08156605 (Ciba), filed May 21, 2008 (corresponding to PCT/EP2009/05564 filed May 11, 2009 and published as WO2009141237 A1), all of which publications are incorporated herein by reference.

This is especially a spiropyran derivative of formula I:

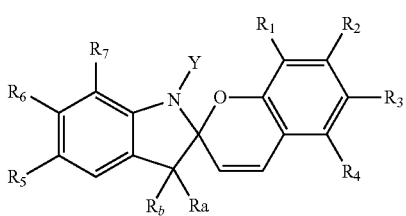

(I)

wherein $R_1$ is hydrogen, —$C_1$-$C_{18}$ alkoxy, —$C_1$-$C_{18}$ alkylthio, halogen, —$C_1$-$C_{18}$ alkyl, —$NO_2$ or a phenyl radical, like preferably phenyl;

$R_2$ is hydrogen, —$C_1$-$C_{18}$ alkoxy or $NO_2$;

$R_3$ is $NO_2$ or halogen;

$R_4$ is hydrogen, —$C_1$-$C_{18}$ alkoxy or halogen;

$R_5$ is hydrogen, halogen, —$C_1$-$C_{18}$ alkoxy, —COOH, —COO—$C_1$-$C_{18}$ alkyl, —$CF_3$ or phenyl;

$R_6$ is hydrogen or $R_6$ and $R_7$ form together a phenyl ring;

$R_7$ is hydrogen;

$R_a$ is hydrogen or —$C_1$-$C_6$ alkyl;

$R_b$ is hydrogen or —$C_1$-$C_6$ alkyl, or together with $R_a$ form a 5-6 membered ring;

Y is phenyl or benzyl wherein the phenyl or benzyl group may be substituted by one or more groups selected from $NO_2$ fluorine, bromine, chlorine, $CF_3$ or phenyl and may carry an annealed benzo ring, or Y is —$CH_2$—COO—$C_1$-$C_{18}$ alkyl or —$CH_2$—COOH or —$CH_2$—CO—N($R_{10}$)—$R_9$; or —$CH_2$—CO—N($R_{10}$)-L-N($R_{10}$) CO—$CH_2$—; wherein $R_9$ is hydrogen, $C_1$-$C_{18}$ alkyl, phenyl, mesityl, phenyl once or more than once substituted by halogen, —$CF_3$, $C_1$-$C_6$ alkyl, —$C_1$-$C_6$ alkoxy, carboxy, —COO—$C_1$-$C_6$ alkyl, —S-phenyl or —CO-phenyl;

$R_{10}$ is hydrogen, $C_1$-$C_{18}$ alkyl;

L is 1,3 phenylene or 1,4 phenylene wherein the phenylene linker is optionally substituted by once or more than once by halogen, —$CF_3$, $C_1$-$C_{18}$ alkyl, —$C_1$-$C_{18}$ alkoxy, carboxy, —COO—$C_1$-$C_{18}$ alkyl, —$CONH_2$, —CON($C_1$-$C_{18}$ alkyl)$_2$, nitro; or L is naphthalene, biphenylene or phenylene-O-phenylene wherein the naphthalene, biphenylene or phenylene-O-phenylene linker is optionally substituted once or more than once by halogen, —$CF_3$, $C_1$-$C_{18}$ alkyl, —$C_1$-$C_{18}$ alkoxy, carboxy, —COO—$C_1$-$C_{18}$ alkyl, —$CONH_2$, —CON($C_1$-$C_{18}$ alkyl)$_2$, nitro.

Phenyl or benzyl Y carrying an is napthyl or napthylmethyl. Preferably, Y does not carry an annealed benzo ring.

Preferences

Preferred are compounds of the formula I wherein $R_1$ is hydrogen, —$C_1$-$C_{18}$ alkoxy, —$C_1$-$C_{18}$ alkylthio, halogen, —$C_1$-$C_{18}$ alkyl or —$NO_2$;

$R_2$ is hydrogen or —$C_1$-$C_{18}$ alkoxy;

$R_3$ is $NO_2$ or halogen;

$R_4$ is hydrogen, —$C_1$-$C_{18}$ alkoxy or halogen;

$R_5$ is hydrogen, halogen, —$C_1$-$C_{18}$ alkoxy, —COOH, —COO—$C_1$-$C_{18}$ alkyl, —$CF_3$ or phenyl;

$R_6$ is hydrogen or $R_6$ and $R_7$ form together a phenyl ring;

$R_7$ is hydrogen;

$R_a$ is hydrogen or —$C_1$-$C_6$ alkyl;

$R_b$ is hydrogen or —$C_1$-$C_6$ alkyl, or together with $R_a$ form a 5-6 membered ring;

Y is phenyl or benzyl wherein the phenyl or benzyl group may be substituted by one or more groups selected from fluorine, bromine, chlorine, $CF_3$ or phenyl or Y is —$CH_2$—COO—$C_1$-$C_{18}$ alkyl or —$CH_2$—COOH or —$CH_2$—CO—N($R_{10}$)—$R_9$; or —$CH_2$—CO—N($R_{10}$)-L-N($R_{10}$) CO—$CH_2$—; wherein $R_9$ is hydrogen, $C_1$-$C_{18}$ alkyl, phenyl, mesityl, phenyl once or more than once substituted by halogen, —$CF_3$, $C_1$-$C_6$ alkyl, —$C_1$-$C_6$ alkoxy, carboxy, —COO—$C_1$-$C_6$ alkyl, —S-phenyl or —CO-phenyl;

$R_{10}$ is hydrogen, $C_1$-$C_{18}$ alkyl;

L is 1,3 phenylene or 1,4 phenylene wherein the phenylene linker is optionally substituted by once or more than once by halogen, —$CF_3$, $C_1$-$C_{18}$ alkyl, —$C_1$-$C_{18}$ alkoxy, carboxy, —COO—$C_1$-$C_{18}$ alkyl, —$CONH_2$, —CON($C_1$-$C_{18}$ alkyl)$_2$, nitro; or L is naphthalene, biphenylene or phenylene-O-phenylene wherein the naphthalene, biphenylene or phenylene-O-phenylene linker is optionally substituted once or more than once by halogen, —$CF_3$, $C_1$-$C_{18}$ alkyl, —$C_1$-$C_{18}$ alkoxy, carboxy, —COO—$C_1$-$C_{18}$ alkyl, —$CONH_2$, —CON($C_1$-$C_{18}$ alkyl)$_2$, nitro.

Preferred are compounds of the formula I wherein Y is

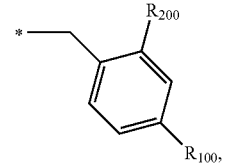

$R_1$ is $C_1$-$C_6$ alkoxy, preferably methoxy, $R_2$ is hydrogen, $R_3$ is $NO_2$, $R_4$ is hydrogen, $R_5$ is hydrogen or $C_1$-$C_6$ alkoxy, $R_6$ is hydrogen, $R_7$ is hydrogen, $R_a$ is methyl, $R_b$ is methyl, $R_{100}$ is $NO_2$, bromine, fluorine or $CF_3$, preferably bromine, fluorine or $CF_3$, $R_{200}$ is hydrogen or fluorine.

Especially preferred is a compound of the formula I wherein
Y is nitro-benzyl, like especially 4-nitro-benzyl, or

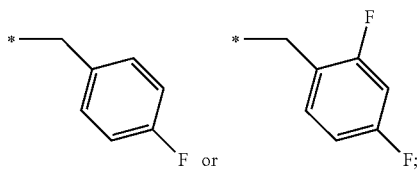

preferably Y is 4-fluoro-benzyl or 2,4-difluoro-benzyl,
$R_1$ is methoxy,
$R_2$ is hydrogen,
$R_3$ is $NO_2$,
$R_4$ is hydrogen,
$R_5$ is hydrogen
$R_6$ is hydrogen,
$R_7$ is hydrogen,
$R_a$ is methyl,
$R_b$ is methyl,
The preferred compound has the following formula

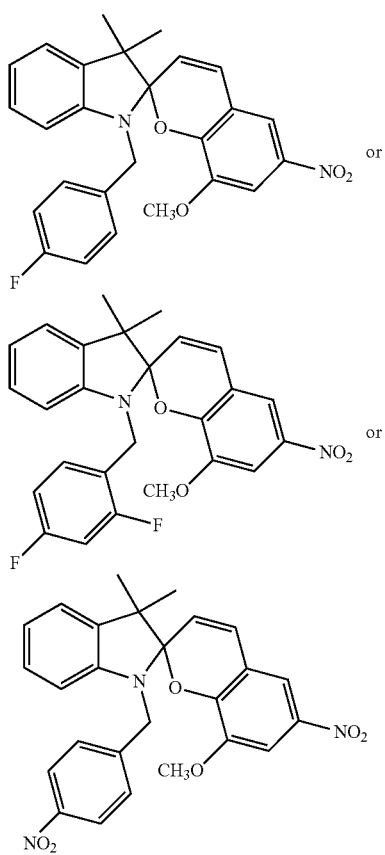

The spiropyran compounds are molten and re-solidified by cooling to room temperature. The re-solidified spiropyran can easily be dispersed in an ink formulation. The milling time is reduced by factor 5 compared to unmolten spiropyrans. The exposure time of the ink formulation by UV radiation is less (approximately 4-40%, preferably 4-10%) compared to an ink formulation containing an unmolten spiropyran.

Furthermore preferred is a compound of the formula I wherein Ra and Rb together form a hexylene ring, Y is phenyl, $R_1$ is methoxy, $R_2$ is hydrogen, $R_3$ is nitro, $R_4$ is hydrogen, $R_5$ is hydrogen, $R_6$ is hydrogen $R_7$ is hydrogen. This preferred compound has the following formula

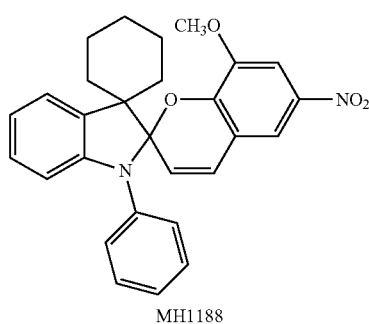

MH1188

Furthermore preferred are compounds of the formula I wherein Y is —$CH_2$—COR,
$R_1$ is $C_1$-$C_6$ alkoxy, $C_1$-$C_6$ alkylthio, or a phenyl radical, like especially phenyl, preferably $R_1$ is $C_1$-$C_6$ alkoxy or $C_1$-$C_6$ alkylthio,
R is —$C_1$-$C_6$ alkoxy or —$NHR_9$ wherein $R_9$ is phenyl, phenyl once or more than once substituted by halogen, —$CF_3$, $C_1$-$C_6$ alkyl, —$C_1$-$C_6$ alkoxy, —S-phenyl or —CO-phenyl,
$R_2$ is hydrogen,
$R_3$ is $NO_2$,
$R_4$ is hydrogen,
$R_5$ is hydrogen,
$R_6$ is hydrogen,
$R_7$ is hydrogen,
$R_a$ is methyl and
$R_b$ is methyl.
These compounds can be expressed by the following formula Ia

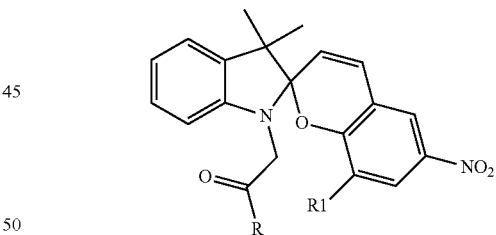

Especially preferred are further compounds of the formula Ia wherein $R_1$ is methoxy or ethoxy and R is

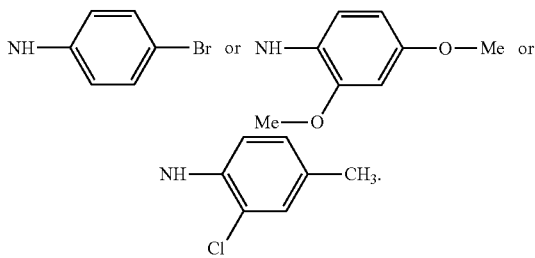

EXAMPLES

Example 1

Melting 1 g 1'-(2,4-Difluorbenzyl),3',3'-dimethyl-6-nitro-8-methoxy(2H-1-benzopyran-2,2'-2H-indol) (LF3233)

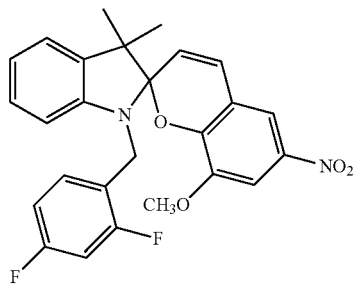

is heated in a glass tube at 160° C. for 5 minutes. The molten mass is cooled to room temperature and pulverized. The powder is then added to an aqueous based basic ink formulation using a planetary mill (available from Fritsch GmbH, Planetary Fritsch Pulverisette 7) to obtain a printing ink.

The basic ink formulation is described below.

The printing ink is then applied to a paper using a wiper. The film thickness is approximately 12 μm. The label obtained is activated using UV light.

The Table below shows that the molten and re-solidified spiropyran according to the invention needs only 1/10 of the UV Dosis to reach the same color strength as the unmolten spiropyran. The radiation time is reduced from 2 seconds to 0.2 seconds.

The values L, a and b used in the present text are informal abbreviations of the coordinates of the CIE color space L*, a* and b* and should not be mixed up with the Hunter values L, a and b. L (and L*) define the lightness axis of the CIE color space with 0 meaning black and 100 meaning white; a (and a*) define the location on the red-green axis (positive values are red, negative values are green, and 0 is neutral); and b (and b*) define the location on the blue-yellow axis (positive values are yellow, negative values are blue, and 0 is neutral).

The starting color values (uncharged) of the unmolten and the molten spiropyran are slightly different due to a slight discoloration during the melting process.

|  | Unmolten 2 seconds activated: | | | molten 0.2 seconds activated: | | |
|---|---|---|---|---|---|---|
|  | L | a | b | L | a | b |
| uncharged | 86.74 | −0.14 | 4.27 | 81.84 | 1.51 | 1.33 |
| charged | 44.6 | −0.54 | −38.43 | 42.36 | −4.94 | −42.01 |

The bleaching kinetic is the same for both products.

The following spiropyrans having a benzylic group Y are treated analogously as described in Example 1.

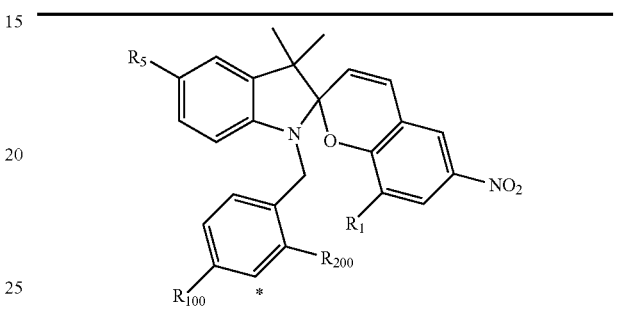

| Lab No. | $R_{100}$ | $R_{200}$ | $R_1$ | $R_5$ | Melting Temp (° C.) | Melting Time (min) | Exposure time to UV radiation (s) | L-value |
|---|---|---|---|---|---|---|---|---|
| LF3206 | Br | H | OMe** | H | — | — | 10 | 53 |
|  |  |  |  |  | 195 | 1 | 4 | 34 |
| LF3391 | H | H | OMe | H | — | — | 10 | 41 |
|  |  |  |  |  | 170 | 1 | 4 | 29 |
| LF2923 | ** | H | OMe | H | — | — | 10 | 56 |
|  |  |  |  |  | 170 | 5 | 4 | 38 |
| LF2807 | F | H | OMe | H | — | — | 10 | 39 |
|  |  |  |  |  | 155 | 1 | 0.4 | 39 |
| FP152 | $CF_3$ | H | OMe | H | — | — | 10 | 27 |
|  |  |  |  |  | 160 | 5 | 10 | 11 |
| FP258 | $CF_3$ | H | OMe | OMe | — | — | 10 | 44 |
|  |  |  |  |  | 160 | 5 | 10 | 16 |
| FP220 | I | H | OMe | H | — | — | 10 | 37 |
|  |  |  |  |  | 185 | 5 | 10 | 22 |

* LF2923 carries a benzo ring which is annealed to the C-atom carrying the substituent $R_{100}$ and the C-atom marked with * in the above formula.
**OMe means methoxy, i.e. $OCH_3$.

The following spiropyrans having an ester or amid group Y are treated analogously as described in Example 1.

| Lab No. | R | $R_1$ | Melting Temp (° C.) | Melting Time (min) | Exposure time to UV radiation (s) | L-value |
|---|---|---|---|---|---|---|
| LF3721 | —OCH(CH$_3$)$_2$ | OMe ($OCH_3$) | — | — | 10 | 31 |
|  |  |  | 150 | 5 | 4 | 14 |

-continued
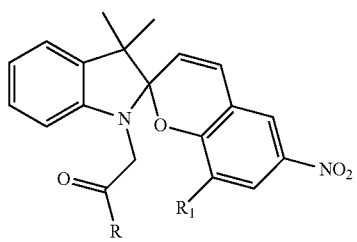
| Lab No. | R | R₁ | Melting Temp (° C.) | Melting Time (min) | Exposure time to UV radiation (s) | L-value |
|---|---|---|---|---|---|---|
| LF3471 | phenyl-NH-R* | OMe | — | — | 10 | 67 |
|  |  |  | 190 | 1 | 4 | 40 |
| LF3838 | 4-Br-phenyl-NH-R* | OMe | — | — | 10 | 63 |
|  |  |  | 180 | 1 | 4 | 38 |
| LF3847 | 2-(phenylthio)phenyl-NH-R* | OMe | — | — | 10 | 85 |
|  |  |  | 180 | 1 | 10 | 50 |
| LF4001 | 2,4-dimethoxyphenyl-NH-R* | OMe | — | — | 10 | 77 |
|  |  |  | 180 | 1 | 1 | 44 |
| LF3849 | 4-methoxyphenyl-NH-R* | OMe | — | — | 10 | 69 |
|  |  |  | 180 | 1 | 1 | 40 |
| LF4005 | 2-chloro-4-methylphenyl-NH-R* | OMe | — | — | 10 | 68 |
|  |  |  | 180 | 1 | 1 | 35 |
| LF4009 | 5-(trifluoromethyl)-2-methoxyphenyl-NH-R* | OMe | — | — | 10 | 77 |
|  |  |  | 180 | 1 | 10 | 43 |
| LF3550 | 2-tert-butylphenyl-NH-R* | OMe | — | — | 10 | 73 |
|  |  |  | 180 | 1 | 4 | 44 |

-continued

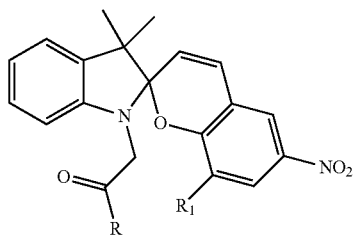

| Lab No. | R | $R_1$ | Melting Temp (° C.) | Melting Time (min) | Exposure time to UV radiation (s) | L-value |
|---|---|---|---|---|---|---|
| LF4022 | (2-Br-4-Me-phenyl)NH-R* | OMe | — | — | 10 | 70 |
|  |  |  | 180 | 1 | 1 | 32 |
| LF4026 | (3-MeO-phenyl)NH-R* | OMe | — | — | 10 | 71 |
|  |  |  | 180 | 1 | 10 | 38 |
| LF4032 | —OCH(CH$_3$)$_2$ | OEt** | — | — | 10 | 82 |
|  |  |  | 180 | 1 | 10 | 55 |
| LF4033 | —OCH(CH$_3$)$_2$ | SMe*** | — | — | 10 | 50 |
|  |  |  | 180 | 1 | 1 | 32 |
| LF4035 | (4-Br-phenyl)NH-R* | OEt** | — | — | 10 | 76 |
|  |  |  | 180 | 1 | 1 | 42 |
| LF4028 | (2-(methoxycarbonyl)phenyl)NH-R* | OMe | — | — | 10 | 76 |
|  |  |  | 180 | 1 | 4 | 59 |
| LF4021 | (2-benzoylphenyl)NH-R* | OMe | — | — | 10 | 74 |
|  |  |  | 180 | 1 | 4 | 61 |

R* indicates the position of the free valency forming the linkage to the rest of the spiropyran molecule.
**OEt = ethoxy = —O—CH$_2$—CH$_3$
***SME = methylthio = —S—CH$_3$ The following spiropyran compound is treated analogously as described in Example 1

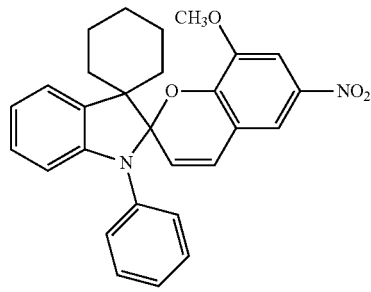

MH118

| | Unmolten 3 seconds activated | | | molten 0.3 seconds activated | | |
|---|---|---|---|---|---|---|
| | L | a | b | L | a | b |
| uncharged | 88.2 | 0.57 | 1.03 | 83.6 | 1.02 | 2.1 |
| charged | 63.6 | 1.05 | 1.8 | 44.17 | −36.96 | −30.53 |

The following spiropyran compound

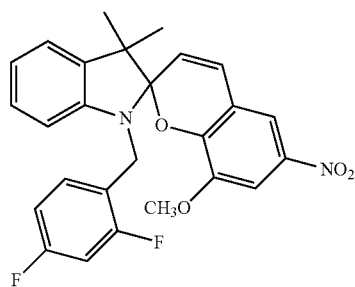

is molten in a glass tube at 171° C. for 5 minutes and further treated according to Example 1.

| | unmolten 2 seconds activated | | | molten 0.2 seconds activated | | |
|---|---|---|---|---|---|---|
| | L | a | b | L | a | b |
| uncharged | 86.74 | −0.14 | 4.27 | 81.84 | 1.51 | 1.33 |
| charged | 44.6 | −0.54 | −38.43 | 42.36 | −4.94 | −42.01 |

A Collin Teachline extruder E 20 T is heated to 160° C. The extruder is loaded with 500 g of the following spiropyran (LF2807)

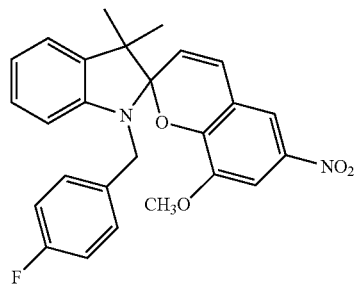

and extruded out in 25 min.

The spiropyran is molten during the extrusion process and exits out as a high viscous liquid which is then cooled. Glassy plates are formed. The plates are crushed and added to an aqueous based basic ink formulation using a planetary mill (available from Fritsch GmbH, Planetary Fritsch Pulverisette 7) to obtain a printing ink.

| | molten 2 seconds activated | | |
|---|---|---|---|
| | L | a | b |
| uncharged | 89.7 | −0.77 | 2.7 |
| charged | 29.97 | −0.57 | −36.95 |

3 g of the following spiropyran

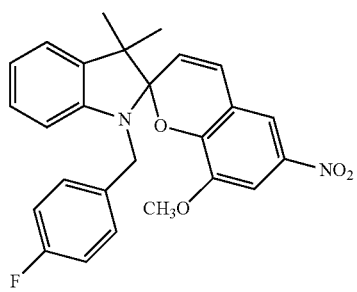

is molten in a microwave (800 W) for 2 minutes. The molten mass is cooled to room temperature and pulverized. The powder is then added to an aqueous based basic ink formulation using a planetary mill (available from Fritsch GmbH, Planetary Fritsch Pulverisette 7) to obtain a printing ink

| molten 2 seconds activated | | | |
|---|---|---|---|
| | L | a | b |
| uncharged | 92.7 | −0.58 | 1.8 |
| charged | 33.4 | −0.62 | −36.73 |

Preparation of the Water Based Printing Ink which Contains 10% Spiropyran (TTI)
Step 1: Basic Printing Ink
  20 g Glascol® LS-16 (Ciba AG) (acrylic copolymer in an aqueous solution)
  20 g Joncryl® 74 (BASF AG)
  0.25 g TEGO® Foamex 845 als antifoaming agent (Evonik Industries AG)
Step 2: Preparation of the TTI-Printing Ink:
  1 g spiropyran (TTI)
  9 g Basic printing ink
  35 g zirconium oxide-balls having a diameter of 0.7-0.9 mm
  Milling for 15 min at 650 rpm (rounds per minute) using a planetary mill (Planetary Fritsch Pulverisette 7 available from Fritsch GmbH, Germany).
Leaving the printing ink over night and separate the balls.

Example 2

Dispersing

The raw, i.e. crystalline and unmilled compound of the formula

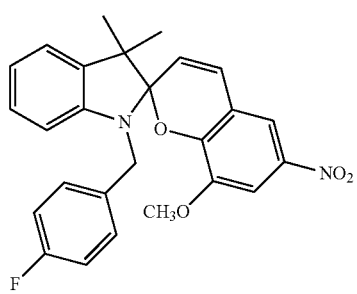

(before melting step) is dispersed in the basic printing ink formulation described above according to the usual dispersion process described above, i.e. using a planetary mill (Planetary Fritsch Pulverisette 7 available from Fritsch GmbH, Germany) and milling at 650 rounds per minute (rpm), and the coloristical properties (especially L-Value→color development) are checked after 5, 15 and 30 minutes dispersion time. The color development after irradiation with UV light (cf. Example 3) is poor and very slow.

| | L | a | b |
|---|---|---|---|
| uncharged | 93.84 | −1 | 2.75 |
| 5' Dispersion | 73.79 | −4.65 | −4.25 |
| 15' Dispersion | 63.79 | −8.72 | −12.72 |
| 30' Dispersion | 59.24 | −7.34 | −10 |

The same compound

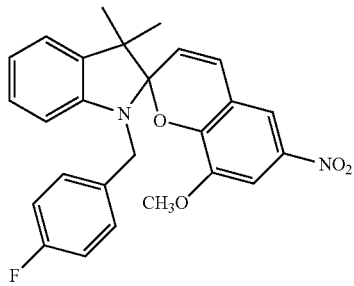

after melting step is also dispersed according to the usual dispersion process and the coloristical properties (especially L-Value→color development) are checked after 5, 15 and 30 minutes dispersion time. The color development after irradiation with UV light (cf. Example 3) shows that a very high and constant L-value is already obtained after only 5 minutes processing time (dispersion time).

| | L | a | b |
|---|---|---|---|
| uncharged | 91.77 | −0.83 | 1.89 |
| 5' Dispersion | 22 | 2.17 | −39.47 |
| 15' Dispersion | 21.74 | 2.83 | −40.97 |
| 30' Dispersion | 22.94 | −1.97 | −37.93 |

Example 3

Color Strength Comparison of Crystalline, Milled and Molten LF2807

Synthesis of crystalline LF2807 (as described on page 19 of WO 2008/083925 A1) having the structure:

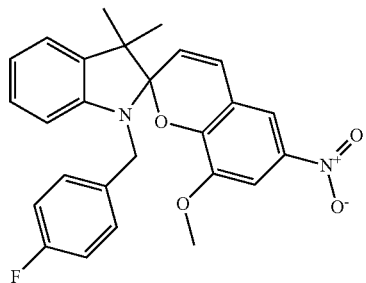

Step 1) A solution of 2,3,3-trimethylindolenine (5.0 g, 31.4 mmol) and 4-fluorobenzylbromide (3.0 g, 15.7 mmol) in dry toluene 30 ml is stirred overnight at 80-85° C. The mixture is cooled to room temperature, filtered through a glass filter, washed with diethyl ether and dried under reduced pressure. The crude product is dissolved in $CH_2Cl_2$ and treated with 5% aqueous NaOH under stirring for 30 minutes. The organic phase is separated, dried over $Na_2SO_4$, passed through a short alumina column in equal parts per volume of hexane-$CH_2Cl_2$ and evaporated giving rise to a corresponding free base, which is immediately dissolved in 10 ml ethanol containing a few drops of triethylamine.

Step 2) A solution of 1-(4'-fluorobenzyl)-3,3-dimethyl-2-methylene-indoline (2.7 g, 10.0 mmol) and 2-hydroxy-3-methoxy-5-nitrobenzaldehyde (3.6 g, 13.0 mmol) is refluxed in 25 ml ethanol for 2 hours, cooled to room temperature, filtered, triturated with 1% triethylamine (in water), washed with water, crystallized from ethanol, and dried under reduced pressure yielding crystalline LF2807.

Color Strength Comparison:

(A): Crystalline LF2807 is stirred in 5% loading in the basic printing ink described above using a standard Teflon made disk-stirrer (100 rpm) for 10 minutes.

(B) Crystalline LF2807 is dispersed and milled in 5% loading in the printing ink described above using a perl mill (pulverisette) with zirconium oxide beads (650 rpm) for 10 minutes.

(C) Crystalline LF2807 is molten, re-solidified, dispersed and milled in 1% loading in the printing ink described above using a perl mill (pulverisette) with zirconium oxide beads (650 rpm) for 10 minutes.

All produced inks are drawn on paper using a #2 doctor blade resulting in an ink thickness of approximately 12 μm (wet). The prints are charged subsequently with UV light of 365 nm for 1 or 10 seconds as specified in the following table and the color is measured using a colorimeter.

The following results are obtained:

| Experiment | starting L-value | Charging | L-value after loading | color strength (approximately) |
|---|---|---|---|---|
| A | 96 | 10 seconds | 91 | extremely low |
| B | 87 | 1 second | 45 | 100%, comparison |
| C | 85 | 1 second | 46 | ~500% |

As can be seen above, after dispersion in the printing ink by identical treatment in the perl mill, the molten, re-solidified and milled LF2807 (Experiment C) exhibits about the same L-value as the unmolten and milled LF2807 (Experiment B) despite the fact that the concentration of the active material in Experiment C is 5 times lower. Therefore the color strength for the molten, re-solidified and milled LF2807 is 500% as compared to the unmolten and milled LF2807 for which the color strength is set as 100%.

The color strength of crystalline LF2807 which is not milled, but only stirred in the printing ink is extremely low.

The invention claimed is:

1. A process to prepare a photochromic ink comprising the steps of:
   a) heating and melting a spiropyran at a temperature below 250° C.,
   b) cooling the melt to obtain a solidified spiropyran,
   c) crushing the solidified spiropyran to obtain a powder, and
   d) adding the powder to a binder providing the basis for the photochromic ink, wherein the spiropyran is a compound of the formula I:

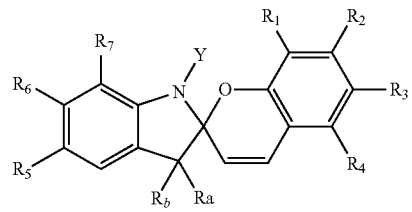

wherein $R_1$ is hydrogen, —$C_1$-$C_{18}$ alkoxy, —$C_1$-$C_{18}$ alkylthio, halogen, —$C_1$-$C_{18}$ alkyl, —$NO_2$ or a phenyl radical, $R_2$ is hydrogen, —$C_1$-$C_{18}$ alkoxy or $NO_2$;

$R_3$ is $NO_2$ or halogen;

$R_4$ is hydrogen, —$C_1$-$C_{18}$ alkoxy or halogen;

$R_5$ is hydrogen, halogen, —$C_1$-$C_{18}$ alkoxy, —COOH, —COO—$C_1$-$C_{18}$ alkyl, —$CF_3$ or phenyl;

$R_6$ is hydrogen or $R_6$ and $R_7$ form together a phenyl ring;

$R_7$ is hydrogen;

$R_a$ is hydrogen or —$C_1$-$C_6$ alkyl;

$R_b$ is hydrogen or —$C_1$-$C_6$ alkyl, or together with $R_a$ form a 5-6 membered ring;

Y is phenyl or benzyl wherein the phenyl or benzyl group may be substituted by one or more groups selected from $NO_2$ fluorine, bromine, chlorine, $CF_3$ or phenyl or Y is —$CH_2$—COO—$C_1$-$C_{18}$ alkyl or —$CH_2$—COOH or —$CH_2$—CO—N($R_{10}$)—$R_9$; or —$CH_2$—CO—N ($R_{10}$)-L-N($R_{10}$) CO—$CH_2$—; wherein $R_9$ is hydrogen, $C_1$-$C_{18}$ alkyl, phenyl, mesityl, phenyl once or more than once substituted by halogen, —$CF_3$, $C_1$-$C_6$ alkyl, —$C_1$-$C_6$ alkoxy, carboxy, —COO—$C_1$-$C_6$ alkyl, —S-phenyl or —CO-phenyl;

$R_{10}$ is hydrogen, $C_1$-$C_{18}$ alkyl;

L is 1,3 phenylene or 1,4 phenylene wherein the phenylene linker is optionally substituted by once or more than once by halogen, —$CF_3$, $C_1$-$C_{18}$ alkyl, —$C_1$-$C_{18}$ alkoxy, carboxy, —COO—$C_1$-$C_{18}$ alkyl, —$CONH_2$, —$CON(C_1$-$C_{18}$ alkyl$)_2$, nitro; or L is naphthalene, biphenylene or phenylene-O-phenylene wherein the naphthalene, biphenylene or phenylene-O-phenylene linker is optionally substituted once or more than once by halogen, —CF$_3$, C$_1$-C$_{18}$ alkyl, —C$_1$-C$_{18}$ alkoxy, carboxy, —COO—C$_1$-C$_{18}$ alkyl, —CONH$_2$, —CON(C$_1$-C$_{18}$ alkyl)$_2$, nitro.

2. The process according to claim 1 wherein the binder is water-soluble or water-dispersible acrylic polymer.

3. The process according to claim 1, wherein the spiropyran is a compound of the formula I wherein
   R$_1$ is hydrogen, —C$_1$-C$_{18}$ alkoxy, —C$_1$-C$_{18}$ alkylthio, halogen, —C$_1$-C$_{18}$ alkyl, or NO$_2$,
   R$_2$ is hydrogen or —C$_1$-C$_{18}$ alkoxy,
   Y is phenyl or benzyl wherein the phenyl or benzyl group may be substituted by one or more groups selected from NO$_2$, fluorine, bromine, chlorine, CF$_3$ or phenyl or
   Y is —CH$_2$—COO—C$_1$-C$_{18}$alkyl or —CH$_2$—COOH or —CH$_2$—CO—N(R$_{10}$)—R$_9$; or —CH$_2$—CO—N(R$_{10}$)-L-N(R$_{10}$)CO—CH$_2$—; wherein R$_9$, R$_{10}$ and L are as defined in claim 1, and
   the remaining substituents are as defined in claim 1.

4. The process according to claim 1, wherein the spiropyran is a compound of the formula I wherein
   Y is

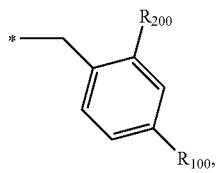

R$_1$ is C$_1$-C$_6$alkoxy, R$_2$ is hydrogen,
R$_3$ is NO$_2$,
R$_4$ is hydrogen,
R$_5$ is hydrogen or C$_1$-C$_6$alkoxy,
R$_6$ is hydrogen,
R$_7$ is hydrogen,
R$_a$ is methyl,
R$_b$ is methyl,
R$_{100}$ is NO$_2$, bromine, fluorine or CF$_3$,
R$_{200}$ is hydrogen or fluorine.

5. The process according to claim 1, wherein the spiropyran is a compound of the formula

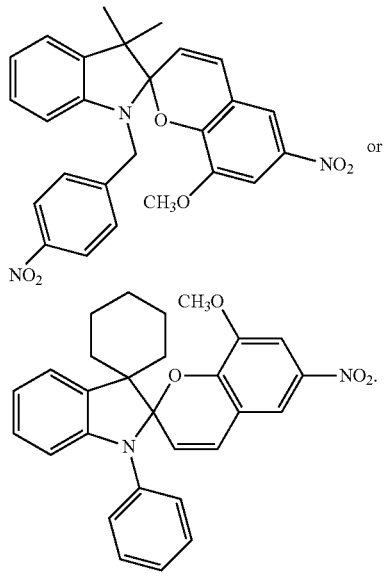

6. The process according to claim 1, wherein the spiropyran is a compound of the formula I wherein
   Y is —CH$_2$—COR
   R$_1$ is C$_1$-C$_6$alkoxy or C$_1$-C$_6$alkylthio
   R is —C$_1$-C$_6$alkoxy or —NHR$_9$ wherein R$_9$ is phenyl, phenyl once or more than once substituted by halogen, —CF$_3$, C$_1$-C$_6$alkyl, —C$_1$-C$_6$ alkoxy, —S-phenyl or —CO-phenyl
   R$_2$ is hydrogen,
   R$_3$ is NO$_2$
   R$_4$ is hydrogen,
   R$_5$ is hydrogen,
   R$_6$ is hydrogen,
   R$_7$ is hydrogen,
   R$_a$ is methyl,
   R$_b$ is methyl.

* * * * *